United States Patent [19]

Hager et al.

[11] Patent Number: 4,783,987

[45] Date of Patent: Nov. 15, 1988

[54] SYSTEM FOR SUSTAINING AND MONITORING THE OSCILLATION OF PIEZOELECTRIC ELEMENTS EXPOSED TO ENERGY-ABSORPTIVE MEDIA

[75] Inventors: Harold E. Hager, Seattle; J. D. Sheldon Danielson, Edmonds, both of Wash.

[73] Assignee: The Board of Regents of the University of Washington, Seattle, Wash.

[21] Appl. No.: 13,133

[22] Filed: Feb. 10, 1987

[51] Int. Cl.[4] .................... G01N 9/00; G01N 11/16
[52] U.S. Cl. ................................ 73/32 A; 73/54; 73/579
[58] Field of Search ........ 73/32 A, 579, 580, DIG. 1, 73/54; 331/65; 324/57 Q, 56, 57 R, 57 SS

[56] References Cited

U.S. PATENT DOCUMENTS

| | | | |
|---|---|---|---|
| 3,710,614 | 1/1973 | Oppliger | 73/59 |
| 4,129,031 | 12/1978 | Tehon et al. | 73/32 A |
| 4,624,129 | 11/1986 | Haynes | 73/32 A |

FOREIGN PATENT DOCUMENTS

950033 1/1983 U.S.S.R. ............... 73/32 A

*Primary Examiner*—Stewart J. Levy
*Assistant Examiner*—Robert P. Bell
*Attorney, Agent, or Firm*—Christensen, O'Connor, Johnson & Kindness

[57] ABSTRACT

The disclosed system includes a piezoelectric crystal exposed to an energy-absorptive medium of interest. A crystal oscillation circuit is included for sustaining oscillation of the crystal in contact with the fluid. To accomplish this, the circuit includes feedback elements for providing automatic gain control of the amplifier portion of the oscillator. In this manner, the conditions required for crystal oscillation are maintained independent of variations in the medium the crystal is exposed to. Information regarding the gain adjustment and oscillation frequency of the crystal are applied to a microprocessor-based system for determining fluid characteristics such as viscosity, density, and dielectric constant. Alternatively, this information is used to correct for the influence of such parameters on the resonant behavior of piezoelectric crystals undergoing mass change, in the analysis of, for example, corrosion, adsorption and electroplating. The relationship between the particular characteristics determined and the output information received from the oscillation circuit is dependent upon the hydrodynamic and electrokinetic coupling experienced between the medium and crystal.

28 Claims, 6 Drawing Sheets

SYSTEM FOR SUSTAINING AND MONITORING THE OSCILLATION OF PIEZOELECTRIC ELEMENTS EXPOSED TO ENERGY-ABSORPTIVE MEDIA

FIELD OF THE INVENTION

This invention relates generally to systems for sustaining and monitoring the oscillation of piezoelectric elements and, more particularly, to systems for sustaining and monitoring the oscillation of piezoelectric elements exposed to energy-absorptive media.

BACKGROUND OF THE INVENTION

The production and use of energy-absorptive media, such as fluids, are widespread elements of modern industrial processing systems. To maintain the integrity of the process involved, it is frequently desirable to monitor particular characteristics of the absorptive medium. This information typically must be accurate and available in real-time, if the process is to be controlled within predetermined parameters of operation. While numerous systems have been developed to analyze the characteristics of absorptive media, such systems are typically relatively expensive. In addition, the response time of existing systems is usually quite slow, making them unsuitable for real-time analysis and control of the operation of an absorptive media processing system.

One recently developed technique of analysis that shows considerable promise, however, involves the use of a piezoelectric quartz crystal exposed to, for example, of fluid of interest. The piezoelectric crystal has a characteristic resonant frequency and, when placed in a lossless environment, will oscillate at that frequency when subject to an alternating electric potential of the same frequency. By exposing the crystal to a fluid of interest, the frequency of oscillation has been shown to decrease by an amount proportional to the density and absolute viscosity of the fluid. Thus, by monitoring the change in the frequency of oscillation observed for a particular liquid of interest placed in contact with the crystal, information about the viscosity and density of the liquid can be produced.

Although this technique of fluid analysis advantageously employs a low-cost crystal sensor to extract real-time information about the fluid or fluid-crystal interface, it is subject to several important limitations. The first of these limitations involves the inadequacy of existing piezoelectric crystal oscillator circuit designs. Traditionally, piezoelectric crystals have been supported for oscillation in relatively lossless environments. An oscillator circuit is then designed to operate the crystal either at its series resonant frequency, where the crystal's impedance is resistive and minimum, or between its series and parallel resonant frequencies where the crystal's impedance is inductive.

In the first case, when the crystal is operated as a resistive element, the effect of an energy-absorptive fluid on the crystal is to increase its resistance to a point at which the resultant energy losses make oscillation difficult to sustain. When the crystal is employed as an inductive element in a filter or matching network, on the other hand, the energy-absorptive fluid impedes oscillation by reducing the quality factor of the crystal, significantly reducing or eliminating its inductive behavior. Although circuits have been developed that are capable of overcoming these difficulties and sustaining the oscillation of a crystal in contact with a relatively energy-absorptive fluid, their use in monitoring fluid characteristics and crystal-fluid interaction has not been satisfactory.

A first problem with existing oscillator circuit designs is that they only produce information regarding the frequency of oscillation of a crystal exposed to an energy-absorptive fluid. Given the numerous fluid characteristics that may influence crystal oscillation, the circuit's use as an analytical tool is severely limited by the availability of only information concerning the oscillation frequency of the crystal exposed to the fluid. Although a vector impedance meter can be used to produce a plot of the magnitude and phase of the crystal impedance that contains substantially all of the information available regarding the crystal's response, the required equipment is prohibitively expensive for most applications and still does not allow real-time analyis of the performance of a fluid processing system to be achieved.

A second problem with existing analysis techniques employing piezoelectric crystals is that the crystal-fluid interface phenomena such techniques are based on have not been completely understood. Because the functional relationship between observable crystal responses to an energy-absorptive fluid and these various crystal-fluid interface phenomena were only partially known, the accuracy and scope of prior art techniques is quite limited. As suggested above, either viscosity or density could be determined by observing the change in the frequency of oscillation of a crystal exposed to an energy-absorptive fluid, but only if the other parameter was known. Similarly, evaluation of mass change phenomena, such as corrosion or adsorption, was limited by the inability to separate such effects from those that arose from the influences of mechanical and electrical fluid parameters.

In light of the foregoing limitations, it would be desirable to develop a relatively simple and inexpensive system that can maintain the oscillation of a piezoelectric element exposed to an energy-absorptive medium. It would also be helpful to extract as much information as possible from the system concerning the effect the medium has on oscillation of the piezoelectric element. The disclosed invention addresses these needs by monitoring multiple parameters of oscillator circuit operation, as well as developing an understanding of crystal-fluid interactions that is sufficiently sophisticated to allow numerous, simultaneously changing fluid characteristics to be monitored.

SUMMARY OF THE INVENTION

In accordance with this invention, a system is disclosed for monitoring the interaction between a piezoelectric element and an energy-absorptive medium of interest that the piezoelectric element is exposed to. The system includes an amplifier connected to the piezoelectric element, causing the piezoelectric element to oscillate while in direct contact with a fluid. The amplifier has an adjustable gain that allows the level of oscillation of the piezoelectric element to be adjusted. A feedback circuit adjusts the gain of the amplifier in response to variations in the interaction between the piezoelectric element and the medium of interest. In this manner, oscillation of the piezoelectric element is sustained. A frequency detection element produces a frequency output signal indicative of the frequency of oscillation of the piezoelectric element. Similarly, a gain-adjustment detection element produces a gain-adjustment output signal indicative of the adjustment in the gain of the amplifier produced by the feedback circuit. Finally, a processing circuit analyzes the frequency output signal and the gain-adjustment output signal to determine a characteristic of interest exhibited by the medium of interest.

In accordance with another aspect of this invention, a method of analyzing an absorptive medium is provided. The method includes the step of exposing a piezoelectric element to the absorptive media. The piezoelectric element is caused to oscillate by connecting the piezoelectric element to an amplifier having an adjustable gain. Then, the gain of the amplifier is adjusted in response to variations in the absorptive medium. Signals indicative of the frequency of oscillation of the piezoelectric element and the adjustment to the gain of the amplifier are produced. Finally, the signals indicative of frequency and gain are analyzed to determine a characteristic of interest exhibited by the absorptive medium.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT OF THE INVENTION

Figure 1:
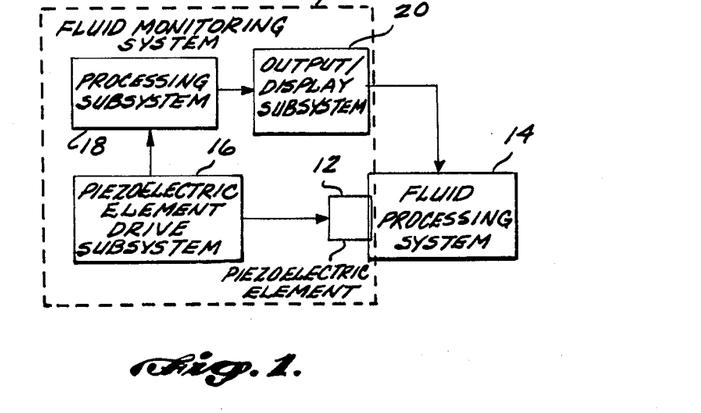
FIG. 1 is a block diagram of a fluid monitoring system employing a piezoelectric element to monitor the characteristics of a fluid contained in a separate fluid processing system.

A system 10 employing a piezoelectric element to monitor various characteristics of an absorptive medium of interest is shown in FIG. 1. As will be discussed in greater detail below, the basic function of system 10 is to oscillate the piezoelectric element when the element is exposed to a medium of interest and monitor the resultant response of the element. Before addressing the details of either system 10 or the piezoelectric element-absorptive medium interface, it should be noted that the practical applications for system 10 are both numerous and diverse.

Broadly speaking, these applications can be characterized as producing either "mass" effects or "apparent mass" effects on the operation of the piezoelectric element. Mass effects are produced when the absorptive medium being analyzed affects the mass of the piezoelectric element. Because the element's mass is a primary determinant of its resonant behavior, mass effects can be detected by monitoring changes in the oscillational characteristics of the piezoelectric element. Thus, with a coating having a mass that is sensitive to a particular characteristic of interest applied to the piezoelectric element, it may be possible to measure that characteristic by observing any changes in the oscillation of the piezoelectric element. For example, the adsorption by the piezoelectric element of gas vapor or dissolved matter in a fluid can be monitored as a mass effect. Similarly, the effect that corrosive fluids have on the mass of the piezoelectric element can be monitored to indicate the fluid's corrosiveness. In addition, the exposure of the piezoelectric element to plating solutions may create a mass effect that can be detected to produce real-time indications of plating thickness.

Unlike true mass effects, apparent mass effects are the result of energy transfer or coupling between the absorptive medium and the piezoelectric element. Numerous classes of piezoelectric element-absorptive medium characteristics lead to such energy transfers, and a variety of practical applications are presented by each class. A first characteristic of interest involves those mechanical properties of the absorptive medium to which the piezoelectric element is exposed that may lead to energy losses from the oscillating piezoelectric element. Fluid viscosity and density are two such mechanical properties that can be determined by monitoring the apparent mass effect of the fluid on the piezoelectric element.

Another class of piezoelectric element-absorptive medium characteristics that contributes to energy transfer involves the electrical properties of the medium. Thus, by monitoring the apparent mass effect of a fluid on an oscillating piezoelectric element, the dielectric constant of the fluid can be determined.

Several miscellaneous characteristics of the medium may also produce apparent mass effects on the oscillation of the piezoelectric element. For example, the presence of absorbed liquids in coatings results in energy losses that allow paints and adhesives to be monitored. Similarly, the reaction phenomena in coatings such as photoresists and epoxies can be monitored as an apparent mass effect for process analysis purposes.

Two final sources of energy transfer between the piezoelectric element and absorptive medium that produce apparent mass effects are temperature differentials or variations at the element-medium interface and variations in hydrostatic pressure. In each case, the apparent mass effect that the energy transfer has on piezoelectric element oscillation may be monitored to determine temperature and pressure variations.

As will be appreciated from the preceding discussion, and as will be discussed in greater detail below, numerous characteristics of the medium and piezoelectric element-medium interface influence the oscillation of the piezoelectric element. The number of these characteristics that can be simultaneously measured is a function of the information available regarding piezoelectric element oscillation. If only one of the characteristics is allowed to vary, it can be measured by monitoring the frequency of oscillation of the piezoelectric element and comparing that frequency with empirically derived data correlating frequency and the characteristic of interest. With additional information available, the number of measurable characteristics can be increased.

For example, if the energy that is required to be applied to the piezoelectric element to sustain oscillation is known, a second characteristic of interest can be simulaneously be measured. In addition, if a pair of identical, expect for specialized treatment, piezoelectric elements are employed, the combined influence of all apparent mass effects on a first element can be used to correct the information obtained from a second element, used to measure a particular true mass effect, for instance, by eliminating the contributory influence that apparent mass effects have on the oscillation of that element. Alternatively, the frequency of oscillation of a single piezoelectric element can be adjusted independent of the characteristics of interest to provide additional information for analysis.

While the preceding paragraphs suggest numerous applications for system 10, the use of piezoelectric element-based analysis is particularly well-adapted to certain applications. For example, processes employing adhesives and photoresists can be monitored with great success by this technique because the evaluation is performed near the solid interface, where fluid and gel properties are most critical.

Turning now to a discussion of the fluid monitoring system 10 of FIG. 1, a piezoelectric element 12 is shown partially exposed to a separate fluid processing system 14. Fluid processing system 14 includes a fluid whose characteristics or interaction with piezoelectric element 12 is to be monitored by system 10. Although the preferred use of system 10 is to monitor the characteristics of fluids, the system can readily be adapted to analyze other energy-absorptive media, such as polymeric coatings or to analyze real mass changes at the surface such as those due to plating or corrosion.

A piezoelectric element drive subsystem 16 is included in monitoring system 10 to sustain the oscillation of the piezoelectric element 12 in contact with the fluid. The drive subsystem 16 also produces output signals, indicative of the interaction between piezoelectric element 12 and the fluid, to a processing subsystem 18 for interpretation. Finally, an output subsystem 20 makes information regarding the characteristics of the fluid and, hence, the interaction between the fluid and piezoelectric element 12, available for use by the operator of system 10 or as a feedback signal applied to fluid processing system 14 for control.

To properly understand the operation of fluid monitoring system 10, the interaction between piezoelectric element 12 and the fluid in fluid processing system 14 must first be understood. Therefore, a more complete description of monitoring system 10 begins with a description of piezoelectric element 12 and its interaction with the fluid in fluid processing system 14. Addressing first the piezoelectric element 12, the basic operational characteristic of element 12 is that it can be mechanically distorted by a voltage applied between select faces of the element. By applying an alternating voltage to element 12 at a frequency that is close to the resonant frequency of the element, element 12 can be operated as an ultrasonic transducer.

Numerous piezoelectric materials are suitable for use in element 12. For example, various types of crystals, ceramics, and polymers may be employed. In the currently preferred embodiment, AT-cut quartz crystals are used because of their relatively low cost and widespread availability.

Figure 2:
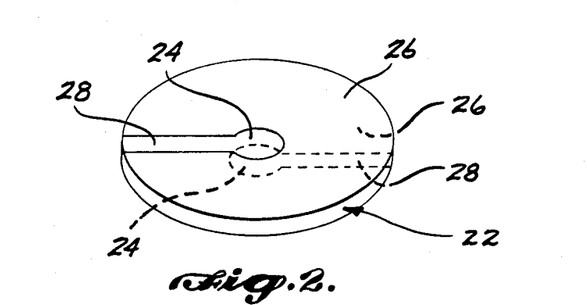
FIG. 2 is an illustration of a piezoelectric crystal constructed for use in conjunction with the system of FIG. 1.

FIG. 2 illustrates a typical wafer-shaped quartz crystal 22 employed as piezoelectric element 12. Crystal 22 is designed to oscillate in the fundamental thickness shear mode at a frequency within the range between 2 MHz and 20 MHz. Circular electrodes 24 of vacuum-deposited silver or aluminum are centered on the opposing circular faces 26 of crystal 22 and have leads 28 extending to opposite edges of the crystal 22. The outer ends of leads 28 are electrically connected to the circuitry of system 10 by mechanical pressure or through the use of conductive cement.

Figure 3:
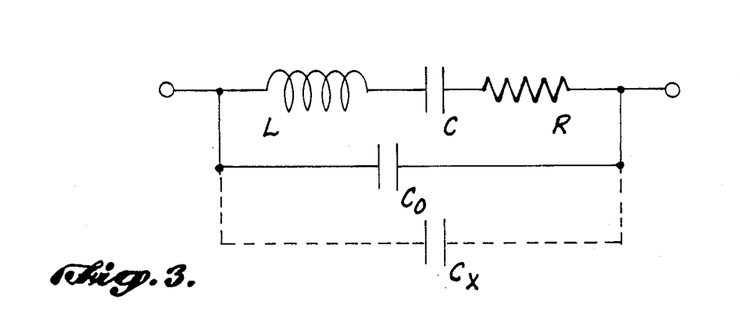
FIG. 3 is an equivalent electrical circuit model of the crystal illustrated in FIG. 2.

To more completely understand the response of crystal 22 to the application of an alternating voltage across its electrodes 24, reference is had to a known electrical equivalent circuit 30 of a piezoelectric element 12, as shown in FIG. 3. The use of equivalent circuit 30 allows mathematical representations of crystal 22 to be formed, enhancing the understanding of various crystal characteristics, as well as offering the ability to predict the influence that crystal characteristics and operation have on the oscillation of crystal 22.

As shown in FIG. 3, equivalent circuit 30 includes five components of interest connected in three parallel branches. In the first branch, an inductive element L represents the motional mass of crystal 22, a resistive element R represents the lumped effect of all the energy losses experienced by crystal 22, and a capacitive element C represents the compliance of crystal 22. In addition to these series-connected components, a parallel capacitive element $C_0$ represents the cpacitance between the electrodes 24 of crystal 22, measured at a frequency sufficiently different from the resonant frequency to justify treating the crystal 22 as a passive dielectric. Another parallel capacitive element $C_X$ may also be included in equivalent circuit 30 to represent the sum of all external capacitances.

Figure 4:
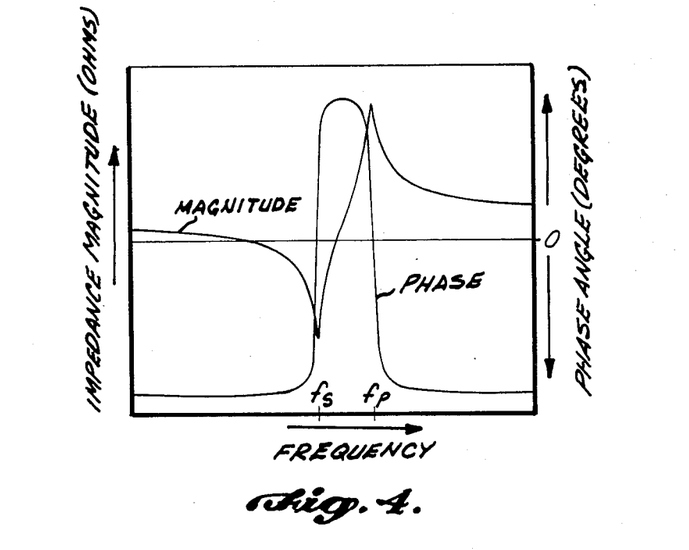
FIG. 4 is a graph of the magnitude and phase angle of the impedance of the crystal, as a function of frequency, when exposed to a relatively lossless environment.

The impedance Z of equivalent circuit 30 is a complex number, having both real and imaginary components, that can be expressed as follows:

$$Z = \left[ \frac{1}{R + j(\omega L - 1/\omega C)} + j\omega C_o \right]^{-1} \quad (1)$$

where $\omega$ is equal to the frequency f of the alternating electrical potential applied to crystal 22 multiplied by the quantity $2\pi$. A representative plot of the magnitude and phase angle of the impedance Z as a function of f is shown in FIG. 4.

As will be appreciated from FIG. 4, there are two frequencies at which the reactive components of the impedance cancel, producing zero phase angle. The lower of these two frequencies is designated the series resonant frequency $f_s$ and when crystal 22 is operated at this frequency its impedance Z is at a minimum value approximately equal to R. The other frequency is identified as the parallel resonant frequency $f_p$ and the impedance Z of a crystal 22 operated at this frequency has a maximum value. Traditional circuits, designed to sustain the oscillation of a piezoelectric crystal in environments that absorb relatively little energy, like air, are generally constructed to operate the crystal at or between one of these two frequencies.

The sharpness of the response curve illustrated in FIG. 4 is defined by a quality factor Q that is proportional to the ratio between the maximum energy stored by the crystal and the energy losses experienced by the crystal per period of input energy. Because a high quality factor indicates that relatively little energy is lost by the crystal, it is easier to sustain the oscillation of a crystal having such a high quality factor. As is discussed in greater detail below, however, the exposure of crystal 22 to most fluids significantly increases energy losses, decreasing the quality factor of the equivalent circuit.

Figure 5:
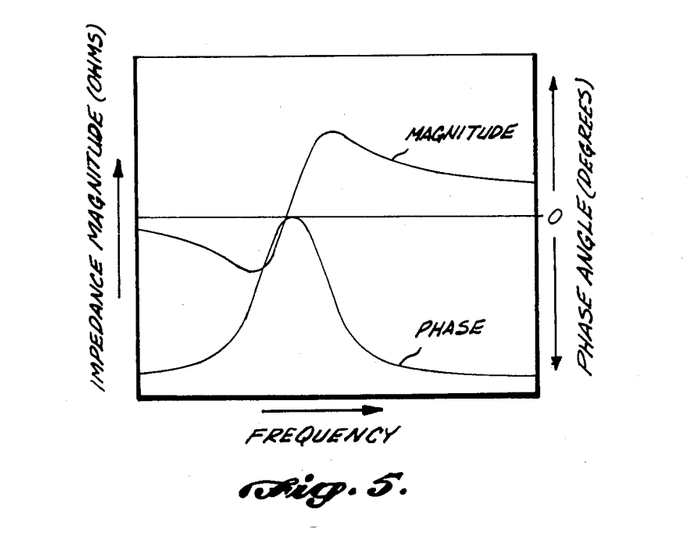
FIG. 5 is a graph of the magnitude and phase angle of the impedance of the crystal, as a function of frequency, when exposed to a relatively energy-absorptive environment.

FIG. 5 representatively illustrates the influence that an energy-absorptive fluid has on the impedance of crystal 22. In comparison to FIG. 4, and with reference to the equivalent circuit 30 illustrated in FIG. 3, the influence of such a fluid is shown to produce a substantial increase in the energy losses or resistance R of the circuit, as well as an increase in the product of the reactive components of the circuit L and C. A more complete understanding of the influence of the fluid on crystal 22 oscillation, however, requires a brief discussion of crystal-fluid interaction.

As a starting point, it should be noted that the following discussion relates primarily to the exposure of crystal 22 to Newtonian fluids. The stress at any point in such fluids is proportional to the time rate of strain at the same point, with the proportionality factor being the viscosity coefficient. A number of fluids do not behave in this manner and eve some otherwise Newtonian fluids exhibit some shear elasticity when operated at frequencies on the order of $10^7$ Hertz. Analysis of such fluids is, accordingly, made more complex.

As discussed previously, the exposure of crystal 22 to an energy-absorptive fluid results in apparent mass effects that make it more difficult to sustain oscillation of crystal 22. To understand and monitor such apparent mass effects, a more detailed review of crystal-fluid interaction is required.

Briefly, the interaction between piezoelectric element 12 and the fluid in processing system 14 results from two phenomena: hydrodynamic coupling and electrokinetic coupling. Hydrodynamic coupling is a result of mechanical properties of the fluid. More particularly, hydrodynamic coupling is a result of the diffusive transport of momentum between the crystal and fluid. Thus, it is primarily determined by the fluid's kinematic viscosity and density.

The physical effect of hydrodynamic coupling is the establishment of an oscillating hydrodynamic boundary layer in the fluid. This layer, having a thickness $\delta_H$, represents the portion of the fluid into which mechanical energy is transferred via diffusion from crystal 22. Fluid within this oscillating hydrodynamic boundary layer can be viewed as being carried by the crystal, creating an apparent mass effect.

While a quantitative analysis of the hydrodynamic coupling between crystal and fluid might be based upon the solution of the classic fluid mechanics problem governing a semi-infinite oscillating plate (Stokes' second problem), that solution is not applicable to situations where the amplitude of the plate's lateral surface displacement varies across the plate. Because the surface displacement and velocity of the oscillating crystal varies across the crystal, it would initially appear that a quantitative analysis of the hydrodynamic coupling between crystal and fluid is more complex. It has been found, however, that the crystal's spatially dependent velocity field has an approximately Gaussian distribution that can be replaced by a spatially independent, "surface-averaged" velocity. This reduces the problem of hydrodynamic coupling between crystal and fluid to Stokes' second problem. indicating that the time-averaged absolute magnitude of the shear $\tau_{xz}$ can be written as:

$$|\tau_{xz}| = 2\mu \delta_N V_S / \pi \qquad (2)$$

where $\mu$ is the viscosity of the fluid and $V_S$ is the surface-averaged velocity.

An important feature of the shear expressed by Equation (2) is that it is the sum of an in-phase shear term and an out-of-phase shear term. The in-phase shear term represents the rate of momentum transfer between the crystal and the fluid boundary layer carried by the crystal. From this term, information regarding the frequency shift caused by the apparent mass effect can be used to determine the fluid's viscosity-density product. More specifically, the effective areal mass density of a fluid, $m_\delta$, is obtained upon dividing $|\tau_{xz}|_{ip}$ by the crystal surface acceleration:

$$\begin{aligned} m\delta &= |\tau_{xz}|_{ip}/V_s\omega \\ &= \pi^{-1}(\mu\rho/2\omega)^{0.5} \end{aligned} \qquad (3)$$

where $\rho$ is the fluid density. The frequency shift $\Delta\omega$ corresponding to this areal mass density is given by the relation:

$$\Delta\omega = -Sm\delta \qquad (4)$$

The sensitivity S is a well-known and computable quantity based on the piezoelectric crystal material and geometry.

The out-of-phase shear term represents the momentum loss to the oscillating hydrodynamic boundary layer via viscous dissipation. The average rate of energy dissipation per unit time, per unit area, $\underline{e}$, is related to the cycle-averaged out-of-phase shear term, $|\tau_{xz}|_{op}$ as follows:

$$\underline{e} = |\tau_{xz}|_{op} V_S \qquad (5)$$

The feedback control circuit yields a gain adjustment signal that is proportional to $\underline{e}$, as described below.

As a final point, the influence of hydrodynamic coupling in two particular crystal-fluid environments should be noted. In the first case, the crystal is exposed to a relative thin liquid coating, having a fixed, uniform thickness. In this situation, the entire fluid layer defines the boundary layer "crried" by the crystal and the resonant frequency of the crystal varies inversely with the total coating mass per unit area. Fluid viscosity plays no significant role.

In the second type of crystal-fluid environment, crystal 22 is exposed to a relatively thick liquid coating of indeterminate depth. The hydrodynamic boundary layer carried by the crystal is less than the thickness of the fluid. This is the more general case and oscillation of crystal 22 is affected by both fluid density and viscosity in the manner described by Equation (2).

The thick-liquid coating environment is preferred when crystal 22 is used as part of a fluid monitoring system for the evaluation of the viscosity-density product. Unlike the thin-coating environment, the coating thickness in this situation does not affect measurement accuracy. Thus, it is easier to make precise measurements of energy transfer between the crystal and fluid.

For accurate separation of viscosity and density it is preferred to employ a fluid thickness that is somewhat less than the thickness of the hydrodynamic boundary layer which would develop in an unlimited volume of the same fluid. This intermediate fluid thickness may be achieved by using a fluid coating with a gas or vapor above the coated crystal. Alternatively, this thickness may be constrained by a chamber wall parallel to the crystal, forming a sample cell between the oscillating crystal and the wall.

The corresponding shear stress and viscous energy dissipation, for a film of thickness F, can be written as:

$$|\underline{\tau}_{xz}| = |\underline{\tau}_{xz}|^{\infty} coth(F/(2\mu/\rho\omega)^{0.5}) \quad (6)$$

$$\underline{e} = e^{\infty} coth(F/(2\mu/\rho\omega)^{0.5}) \quad (7)$$

Here the superscript $\infty$ terms represent the results obtained for the case of very large separation distances. Because of the influence of the fluid's dielectric constant, $\epsilon$, upon the distribution of motion on the crystal surface, the hydrodynamic coupling is dependent on $\epsilon$ as well as the fluid mechanical parameters. Thus, the difference in gain adjustment (AGC) and $\omega$ between two fluids is given by $$\Delta AGC = -k_1(\Delta(\rho\mu)^{0.5} + f(\Delta\epsilon)) \quad (8)$$

$$\Delta\omega = -k_2\Delta(\rho\mu)^{0.5} + g(\Delta\epsilon) \quad (9)$$

Three points can be made regarding Equations (8) and (9). First, both functions f and g are for a wide range of fluids approximately linearly dependent on changes of the solution dielectric constant, $\Delta\epsilon$. In addition, f and g are influenced strongly by the crystal electrode geometry. Second, compensating effects reduce the relative dependence of dielectric constant influence on $\Delta AGC$. Finally, Equations (8) and (9) represent two equations in two unknowns, $\Delta\epsilon$ and $\Delta(\rho\mu)^{0.5}$, allowing quantitative evaluation of the viscosity-density product in solutions of unknown $\epsilon$.

Turning now to a discussion of the second form of crystal-fluid interaction, electrokinetic coupling is a result of the electrical properties of the fluid and the crystal-fluid interface. Examples of such properties are the ionic strength and dielectric constant of the fluid. Electrokinetic coupling arises from the interplay between an interfacial fluid velocity v, defined relative to the crystal's surface, and the fluid's charge density $\rho_e$.

More particularly, the product of fluid velocity and charge density represents a local current density that defines a streaming current. Transient local variations in the streaming current create changes in the charge density distribution, resulting in an induced streaming potential. The streaming potential establishes a flux of ions having a vector sign opposite to that of the streaming current. It is the product of this streaming potential and streaming current that defines the electrical coupling term.

As with the analysis of hydrodynamic coupling, variations in surface velocity patterns over the crystal make the electrokinetic coupling term somewhat difficult to characterize. To overcome this difficulty, it is possible to represent the velocity as having an approximately Gaussian distribution that can be replaced by a spatially independent, surface-averaged velocity. Even so, accurate analysis of the electrokinetic coupling term as discussed below is limited to potential of zero charge (PZC) conditions, which correspond to minimum electrokinetic coupling. With more accurate definitions of surface velocity pattern variations, however, quantitative assessment of the electrokinetic coupling effect will be available.

Figure 6:
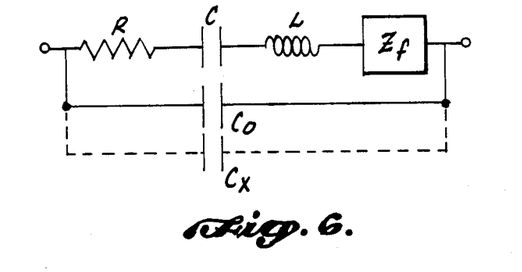
FIG. 6 is an electrical circuit equivalent of a piezoelectric crystal exposed to an energy-absorptive medium.

Having briefly reviewed the two major forms of coupling, or energy loss, between crystal 22 and the fluid of processing system 14, a more detailed consideration of the influence that the fluid has on the equivalent circuit 30 of the crystal 22, as shown in FIG. 3, is provided. As shown in FIG. 6, a more complete model includes an impedance element $Z_F$, representative of the impedance contribution of the fluid, in the series R-L-C branch of circuit 30. As will be appreciated, the impedance Z of the resultant equivalent circuit 32 can be expressed as:

$$Z = \left[ \frac{1}{R + j(\omega L - 1/\omega c) + Z_f} + j\omega C_o \right]^{-1} \quad (10)$$

In contrast to the model of equivalent circuit 30, inclusion of the impedance element $Z_F$ in equivalent circuit 32 makes it unnecessary to collectively include the influence of viscous coupling within the inductive and capacitive elements L and C.

Figure 7:
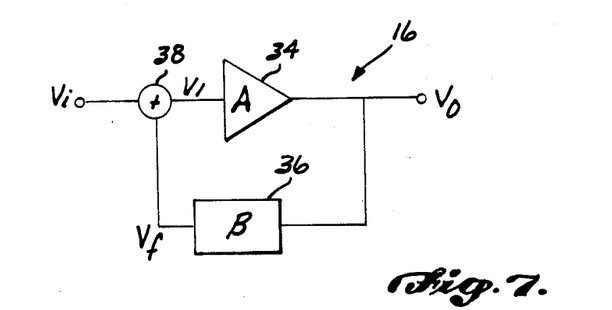
FIG. 7 is a block diagram of a feedback system employed by the system of FIG. 1 to sustain oscillation of a piezoelectric element in contact with a fluid.

Given the preceding discussion of the interaction between piezoelectric element 12 and the fluid in processing system 14, it will be appreciated that the coupling or energy losses involved tend to damp oscillation and/or produce changes in the frequency of crystal oscillation. A basic block diagram of the piezoelectric element drive subsystem 16 of monitoring system 10 used to sustain oscillation of piezoelectric element 12 under such conditions is shown in FIG. 7.

As shown, drive subsystem 16 includes an amplifier 34, feedback network 36, and summing circuit 38. Briefly, amplifier 34 amplifies the output $V_1$ of summing circuit 38 by a gain a to produce an output voltage $V_0$. Feedback network 36 receives the output voltage $V_0$ and produces a feedback voltage $V_F$ that is equal to the product of the output voltage $V_0$ and the transfer function $\beta$ of network 36. The sum of $V_I$ and $V_F$, designated $V_1$, is produced at summing circuit 38 for input to amplifier 34.

The loop gain of subsystem 16 is defined by the product of the terms A and $\beta$. As this loop gain approaches $+1$, the ratio of the output voltage $V_0$ to the input voltage $V_i$ approaches infinity, allowing the circuit to oscillate. Given that A and $\beta$ are complex, frequency-dependent quantities and that oscillation can only take place if the vector product of A and $\beta$ is $+1$, the product of the magnitude of each term must be equal to $+1$, while the sum of the angles of each term equal 0. Thus, the product of the amplifier gain A and feedback transfer function $\beta$ must be sufficient to satisfy these criteria if the oscillation of a crystal 22 exposed to fluid in processing system 14 is to be sustained.

Figure 8:
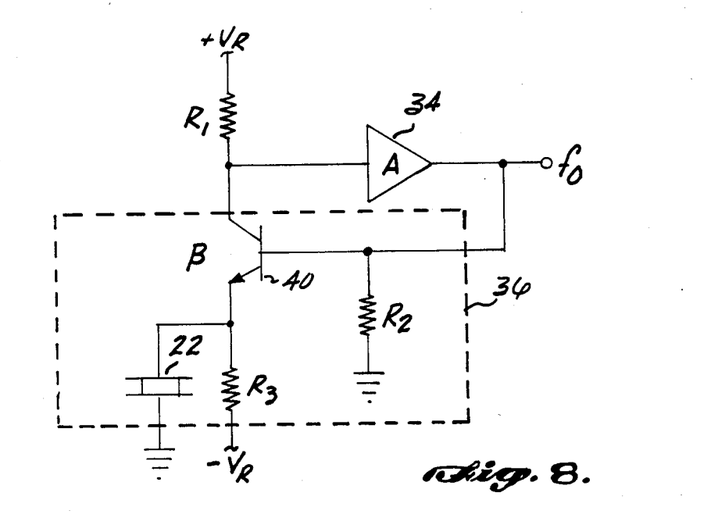
FIG. 8 is a more detailed block diagram of one embodiment of the feedback system of FIG. 7.

To better understand the oscillatory response of a piezoelectric crystal included in a positive feedback network, reference is had to the relatively simple feedback system shown in FIG. 8. There, an NPN bipolar transistor 40 has its collector connected to the input of amplifier 34 and to a $+V_R$ voltage source via resistor $R_1$. The base of transistor 40 is connected to the output of amplifier 34 and to ground by a second resistor $R_2$. Finally, the emitter of transistor 40 is connected to a $-V_R$ voltage source through a third resistor $R_3$ and to ground through crystal 22.

The transfer function $\beta$ of the resultant feedback network can be approximated as:

$$\beta = \frac{-R_1}{Z_c + R_E} \quad (11)$$

where $Z_C$ is the impedance of the parallel combination of crystal 22 and resistance $R_3$ and $R_3$ is a quantity derived from the h-parameter model of the circuit that is inversely proportional to the DC emitter current of transistor 40. This results in a gain of the circuit that is, within limits, proportional to the reciprocal of $Z_E$ and, thus, the gain will be a maximum when the crystal 22 is in series resonance.

Figure 9:
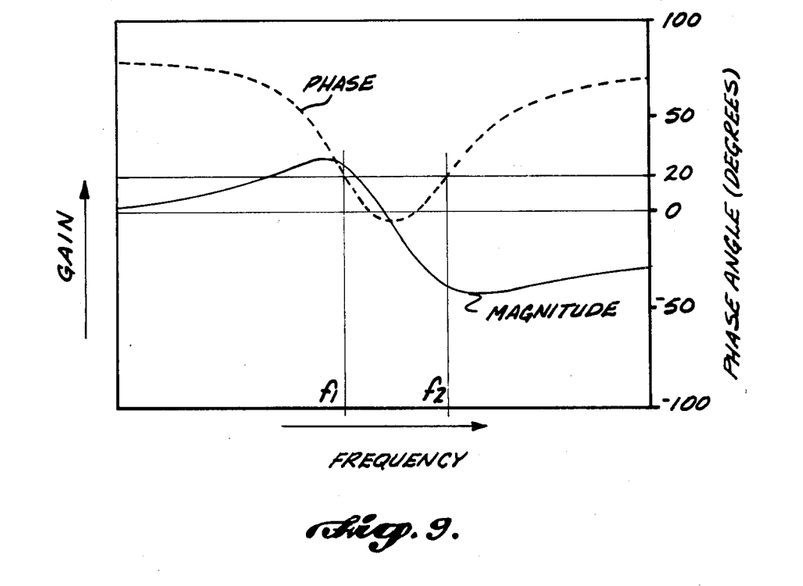
FIG. 9 is a graph of the magnitude and phase angle of the transfer function of the feedback system illustrated in FIG. 8.

The frequency of oscillation of the crystal 22 employed in the circuit of FIG. 8 can be determined in the following manner. As noted previously, to sustain oscillation, the sum of the phase angles of the complex gain A and complex feedback transfer function $\beta$ must be equal to zero. Assuming, for example, that amplifier 34 introduces a phase lag of 20 degrees into the signal passing therethrough, the two-port network of transistor 40 and crystal 22 must introduce a cancelling phase lead of 20 degrees to maintain oscillation. As shown in the graph of the magnitude and phase angle of the transfer function of this two-port network (FIG. 9), this requirement is satisfied at two frequencies of operation designated $f_1$ and $f_2$. Typically, crystal 22 will oscillate at the frequency having the higher gain associated therewith, which in FIG. 9 is $f_1$. As will be appreciated, if the phase shift introduced by amplifier 34 alters, the corrective phase shift initiated by the transistor 40 and crystal 22 will cause the frequency of oscillation of crystal 22 to change. In a particular embodiment of the invention described in greater detail below, this phenomena allows additional information about fluid characteristics or crystal-fluid interaction to be extracted.

Figure 10:
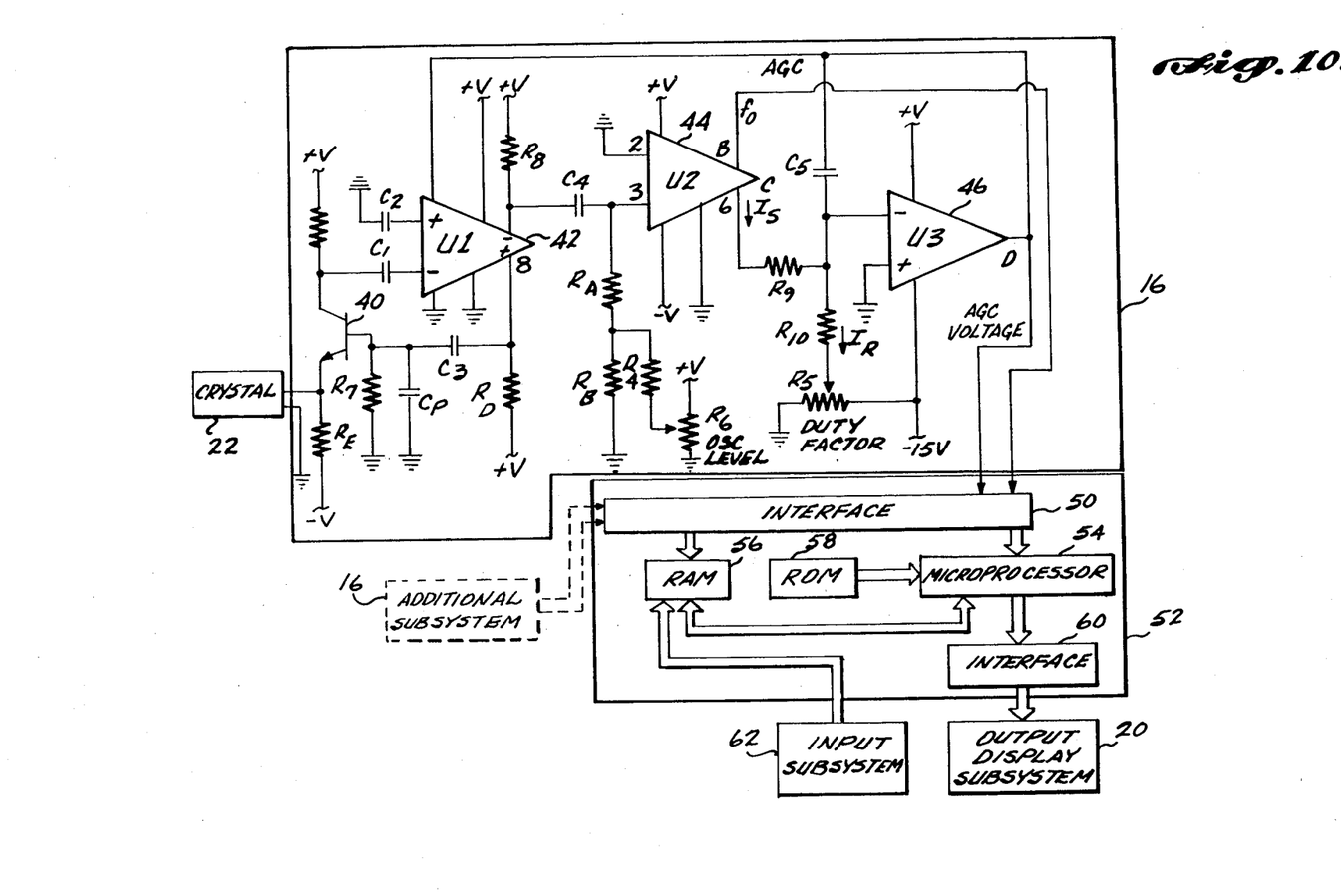
FIG. 10 is a more detailed diagram of another embodiment of the feedback system of FIG. 7, including the other components of the monitoring system illustrated in FIG. 1.

Although the circuit illustrated in FIG. 8 is helpful to illustrate the manner in which the frequency of crystal oscillation is determined, it suffers an important disadvantage that limits its utility in most practical applications. More particularly, only information concerning the frequency of oscillation is available. To address this problem, a new circuit has been developed for producing the desired feedback-controlled oscillation of piezoelectric element 12 and is shown in FIG. 10 as part of a complete monitoring system 10. Basically, this circuit can be considered to include three sections.

In the first section, the crystal 22 and an NPN transistor 40 are shown connected in a positive feedback loop with an intermediate frequency (IF) amplifier (U1) 42. More particularly, the collector of transistor 40 is connected to a $+V$ voltage source through resistor $R_C$ and to a negative input of amplifier 42 by a capacitor $C_1$. The base of transistor 40 is connected to the positive output of amplifier 42 by a capacitor $C_3$ and to ground by a capacitor $C_p$ and resistor $R_7$. The positive output of amplifier 42 is also connected to a $+V$ voltage source via $R_D$. Finally, the emitter of transistor 40 is connected to ground via crystal 22 and to a $-V$ voltage source via resistor $R_E$.

The function of this section is substantially the same as that described in conjunction with the circuit of FIG. 8. More particularly, an oscillator is defined, with transistor 70 and crystal 22 producing a phase shift that cancels the phase shift introduced by amplifier 42, thus satisfying one of the requisites for oscillation. Resistors $R_C$, $R_7$ and $R_E$ correspond to resistors $R_1$, $R_2$, and $R_3$, respectively. Capacitors $C_1$, $C_2$ (connected to the positive input of amplifier 42), and $C_3$ are all coupling capacitors, while capacitor $C_P$ is included to allow the phase shift of amplifier 42 to be adjusted in a manner, and for a reason, described in greater detail below. Amplifier 42 is conveniently provided by the Motorola integrated circuit designated MC1350P.

A second section of the circuit of FIG. 10 includes a comparator (U2) 44 that receives the signal from the negative output of amplifier 42 via a coupling capacitor $C_4$. Comparator 44 is preferably a differential-input, complementary-output, high-speed device, such as National Semiconductor integrated circuit LM360, which performs two functions. First, comparator 44 converts the sinusoidal analog output of amplifier 42 into a digital signal from which the oscillation frequency can be more easily determined. A frequency output from comparator 44 is shown at point B in the circuit, allowing this to be accomplished.

The second function of comparator 44 is to perform a level measurement that can be used to initiate the gain adjustments necessary to sustain oscillation of crystal 22 when changes in the fluid loading of crystal 22 result in crystal impedance variations. Basically, the oscillating output of amplifier 42 is provided to one of the differential inputs of comparator 44, superimposed upon a uniform bias signal. The digital output of comparator 44 remains high unless the sum of the oscillating signal and the bias signal is negative. Thus, the duty factor of the signal produced, as well as its time-averaged value, is dependent on the amplitude of the signal received from amplifier 42.

Figure 11A:
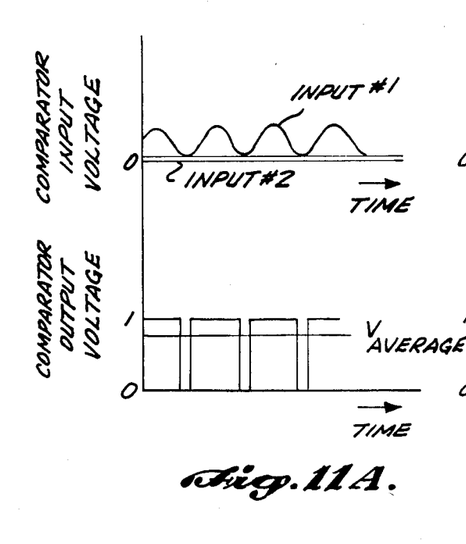
FIGS. 11A and 11B are illustrations of the input and output signals applied to and received from a comparator included in the system of FIG. 9.
Figure 11B:
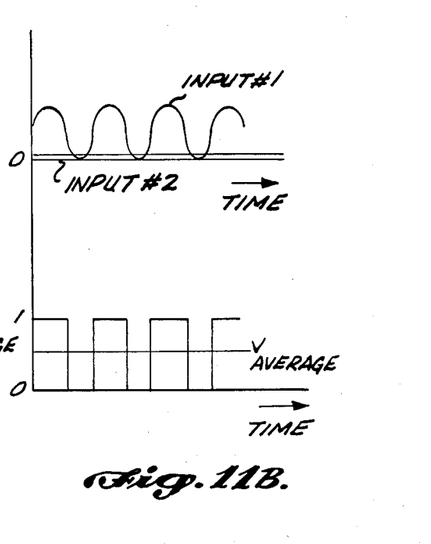

To more clearly appreciate the relationship between the output of amplifier 42 and the duty factor and average value of the comparator output, reference is had to FIGS. 11A and 11B. FIG. 11A provides an illustrative comparison of the inputs and output of comparator 44 when the output of amplifier 42 is relatively low. In FIG. 11B, a similar comparison of comparator inputs and output is made for a relatively large amplifier 42 output. As is clearly indicated, when the positively biased oscillation level of amplifier 42 is large, its negative peaks create a longer interval during which the output of comparator 44 is low. Thus, the duty cycle of the comparator is lower for this situation, as is the averge voltage produced.

To alter the duty cycle produced for a given output of amplifier 42, the bias signal applied to the differential input of comparator 44 can be adjusted, for example, by adjusting the voltage drop with a potentiometer $R_6$. Potentiometer $R_6$ is connected to the input by one resistor $R_4$, included in a voltage divider with $R_B$, and a second resistor $R_A$.

The output of comparator 44 is provided to the third section of the circuit via resistor $R_9$ in the form of a current $I_S$ whose level is determined by the voltage drop across resistor $R_9$ and which is proportional to the duty factor indicated at point C. The difference between the current $I_S$ and a reference current $I_R$, developed by resistor $R_{10}$ and potentiometer $R_5$, is integrated by an integrator defined by operational amplifier 46 and an integrating capacitor $C_5$. Amplifier 46 is suitably provided by the integrated circuit designated CA3140 and produced by RCA. The integrated differential developed by amplifier 46 and capacitor $C_5$ is then applied via a second negative feedback loop to the AGC input of IF amplifier 42.

As will be appreciated, if the oscillatory output of amplifier 42 is originally relatively small, the output of comparator 42 will have a relatively large duty cycle, resulting in the application of a large current to the input of the integrator formed by capacitor $C_5$ and amplifier 46. As a result, the output of the integrator will be reduced. This reduced signal, when applied to amplifier 42 via the feedback loop, increases the gain and oscillation level of amplifier 42. By adjusting the reference current applied to integrator 46, for example, with potentiometer $R_5$, the duty cycle can be controlled.

As will be appreciated, the automatic gain control (AGC) output of operational amplifier 46 at point D allows the loop gain $A\beta$ of the circuit to be maintained at a level exactly equal to $+1$, independent of changes in the gain of amplifier 42 with time or temperature, changes in the resonant impedance of the crystal 22, or substitution of different crystals 22 in the circuit.

Turning now to the manner in which the various outputs of the above-described circuits are analyzed by processing subsystem 18, reference is again had to FIG. 10. The outputs provided at points B and D are applied to an input interface 50 of a microcomputer 52. Thus, the oscillation frequency and automatic gain control signals are made available for analysis by a microprocessor 54 included in microcomputer 52. As shown in FIG. 10, input information received by interface 50 may be stored in random access memory (RAM) 56 or supplied directly to microprocessor 54. Microprocessor 54 analyzes this information in accordance with program instructions stored in a read-only memory (ROM) 58 included in microcomputer 52.

Figure 12:
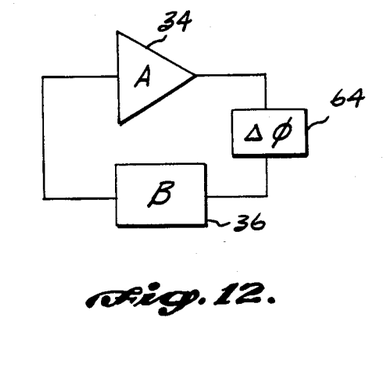
FIG. 12 is an alternative embodiment of the feedback system of FIG. 7, including a phase-shift element to alter the response of the feedback system.

As noted previously and discussed in greater detail below, the ability to measure multiple parameters of the fluid and crystal-fluid interface is dependent upon the amount of information available regarding crystal oscillation. While the basic circuit described in connection with FIG. 10 effectively doubles the information previously available, several methods of employing this circuit to produce more extensive information can be adopted. For example, a digital phase shifter 64 can be included in the basic feedback system of FIG. 7, as shown in FIG. 12, or between capacitors $C_P$ and $C_3$ of the more detailed circuit illustrated in FIG. 10. As will be appreciated from the previous discussion of FIG. 9, by providing desired adjustments in the phase shift originally introduced by amplifier 34, phase shifter 64 causes the combined transistor 40 and crystal 22 to institute cancelling phase shifts, which shift the operating frequency of oscillation of crystal 22. Thus, under substantially fixed crystal-fluid conditions, the gain control and oscillation frequency information available from circuit 16 can be produced for various points along the crystal's impedance curve, allowing a relatively complete description of crystal oscillation to be produced.

As will be appreciated from the preceding discussion, analysis of the automatic gain control signal, which compensates for absorptive media losses, along with the oscillation frequency of the crystal, allows microprocessor 54 to effectively monitor impedance variations of the crystal-media environment. More particularly, the software in ROM 58 can be designed to instruct microprocessor 54 to perform an updated impedance assessment by determining an empirically derived impedance associated with the gain and frequency adjustments from a look-up table stored in ROM 58.

When a more complete description of the frequency dependence of the crystal's impedance is made available to microprocessor 54 by the phase-shifting technique described above, the possibility of modeling the equivalent circuit parameters of the crystal, illustrated in FIGS. 3 and 6, for use in a predictive analysis of the crystal's response to changing parameters is presented. For example, the program instructions in ROM 58 may cause microprocessor 54 to perform a numerical analysis of the data to yield approximations of the equivalent circuit parameters. Once determined, the equivalent circuit parameters can be stored in RAM 56 and recalled by microprocessor 54 for subsequent use.

The instructions stored in ROM 58 may also direct microprocessor 54 to analyze the various hydrodynamic and electrokinetic coupling effects described above. For example, with the solution to Stokes' second problem stored in ROM 58 via Equations 2, 3, 4, and 5, and the appropriate coefficients initialized in RAM 56 via a user input subsystem 62, microprocessor 54 can retrieve the information concerning frequency of oscillation and gain control stored in RAM 56 to determine the viscosity-density product of the energy-absorptive medium crystal 22 is exposed to.

In certain applications where the hydrodynamic coupling effects and true mass effects can be maintained constant, microprocessor 54 may be instructed by software in ROM 58 to identify the existence of PZC conditions where electrokinetic coupling is at a minimum. More particularly, if RAM 58 instructs microprocessor 54 to institute an electrochemical potential change the oscillation of crystal 22 can be continuously monitored to determine the occurrence of a frequency maximum. Minimum coupling occurs at this point, indicating that PZC conditions are in existence.

In another application, user input subsystem 62 may be used to indicate that microprocessor 54 is to analyze the crystal-fluid interaction under predetermined thin-liquid coating conditions. In that case, microprocessor 54 receives instructions from ROM 58 which cause it to access a function table stored in ROM 58 containing empirically derived information correlating the frequency of oscillation of crystal 22 with the total coating mass, per unit area, of the fluid. In this manner, microprocessor 54 is able to produce an indication of the density of the fluid from the frequency response of the crystal stored in RAM 56 and initialized information regarding thin-liquid coating conditions such as fluid thickness, when thickness is physically controlled.

A final particularly useful application, suggested previously, involves the determination of a particular true mass effect of interest, with the interfering influence of apparent mass effects eliminated. To accomplish this, a coating having a known mass, and known response to a particular characteristic of the fluid that is of interest, can be applied to the crystal 22. Assuming that true mass effects are only the result of that single characteristic of interest, the gain-adjustment and oscillation frequency information produced by circuit 16 will be a function of both the particular characteristics of interest and the combined influence of all apparent mass effects. If a second oscillator circuit 16 is established, as shown in dotted lines in FIG. 10, employing a crystal 22 that is substantially identical to the one in the first circuit, except lacking the select coating, its output can also be applied to the input interface 50 of microcomputer 52. Because this output is representative of the cumulative apparent mass effects of the fluid on crystal oscillation, it can be used to correct the information produced for the oscillation of the first crystal, leaving only information indicative of the true mass effect of interest. By comparing the corrected signal with empirically derived data stored in a look-up table in ROM 58, the microprocessor is thus able to measure the desired characteristics of interest.

Regardless of the particular ROM 58 instructions performed by microprocessor 54, the information produced concerning crystal-media interaction is applied to an output interface 64 for transmission from microcomputer 52. As shown, the output subsystem 20 receives this information for use in a variety of ways. Depending upon the particular application in which fluid monitoring system 10 is employed, subsystem 20 may produce a record of fluid variations, such as viscosity and density changes. Similarly, an output may be provided directly to the operator monitoring system 10 or processing system 14.

Given the real-time availability of information from monitoring system 10, however, perhaps the most useful application of output subsystem 20 is the provision of feedback control to the processing subsystem 14. For example, with microprocessor 54 instructed to determine the viscosity of a fluid being produced by system 14, signals indicative of changes in viscosity can be applied to processing system 14, where the necessary adjustment in component chemicals or processing techniques can be effected to ensure that viscosity remains within a predetermined range.

Those skilled in the art will recognize that the embodiments of the invention disclosed herein are exemplary in nature and that varios changes can be made therein without departing from the scope of the spirit of the invention. In this regard, and as was previously mentioned, the invention is readily embodied with various materials and constructions employed for piezoelectric element 12. In addition, various feedback circuit alterations can be made, while still producing the necessary gain and phase feedback adjustments. The manner in which the information produced by the circuit is monitored can also be varied to yield information in any particular desired, useful format. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A system for monitoring the interaction between a piezoelectric element and an energy-absorptive medium of interest that said piezoelectric element is exposed to, said system comprising:

an amplifier, connected to said piezoelectric element, said amplifier causing said piezoelectric element to oscillate when said piezoelectric element is connected thereto, said amplifier having an adjustable gain that allows the level of oscillation of said piezoelectric element to be adjusted;

feedback means for adjusting said gain of said amplifier, in response to variations in the electrical characteristics of said piezoelectric element produced by variations in the interaction between said piezoelectric element and said medium of interest, to sustain the oscillation of said piezoelectric element;

frequency output means for producing a frequency output signal indicative of the frequency of oscillation of said piezoelectric element;

gain-adjustment output means for producing a gain-adjustment output signal indicative of the adjustment in said gain of said amplifier produced by said feedback means;

processing means for analyzing said frequency output signal and said gain-adjustment output signal to determine a characteristic of interest exhibited by the medium of interest.

2. The system of claim 1, further comprising characteristic output means for producing a characteristic output signal indicative of said characteristic of interest determined by said processing means.

3. The system of claim 2, wherein said energy-absorptive media is a fluid being processed by a fluid processing system.

4. The system of claim 3, wherein said characteristic of interest is the viscosity-density product of said fluid.

5. The system of claim 3, wherein said characteristic of interest is the dielectric constant of said fluid.

6. The system of claim 3, wherein said characteristic of interest is the effect said fluid has on the mass of said piezoelectric element.

7. The system of claim 3, further comprising display means for receiving said characteristic output signal and producing a display indicative of said characteristic of interest.

8. The system of claim 3, further comprising control means for producing a control signal in response to said characteristic output signal, said control signal being supplied to said fluid processing system to adjust the processing of said fluid.

9. The system of clai 1, wherein said gain of said amplifier is representable by a complex number and said feedback means is representable by a transfer function that is a complex number, the product of the magnitudes of said gain and said transfer function being maintained substantially equal to positive one and the sum of the phase components of said gain and said transfer function being maintained substantially equal to zero by said feedback means.

10. The system of claim 9, further comprising phase shift adjustment means for controllably adjusting the phase angle of said amplifier to cause the frequency of oscillation of said piezoelectric element to shift.

11. The system of claim 10, wherein said processing means comprises a microprocessor for analyzing said frequency output signal and said gain-adjustment output signal at a plurality of frequencies of oscillation produced by said phase shift adjustment means.

12. A method of analyzing an absorptive medium comprising the steps of:

exposing a piezoelectric element to said absorptive medium;

causing said piezoelectric element to oscillate by connecting said piezoelectric element to an amplifier having an adjustable gain;

adjusting the gain of said amplifier in response to variations in the electrical characteristics of said piezoelectric element produced by variations in said absorptive medium;

producing a signal indicative of the frequency of oscillation of said piezoelectric element;

producing a signal indicative of the adjustment made to the gain of said amplifier; and, analyzing said signals indicative of the frequency of oscillation of the piezoelectric element and the adjustment to the gain of said amplifier to determine a first characteristic of interest exhibited by said absorptive medium.

13. The method of claim 12, further comprising the step of producing a display indicative of the characteristic of interest.

14. The method of claim 12, wherein said characteristic of interest is the viscosity-density product of said absorptive medium.

15. The method of claim 12, wherein said characteristic of interest is the dielectric constant of said absorptive media.

16. The method of claim 12, wherein said characteristic of interest is the effect said medium has on the mass of the piezoelectric element.

17. The method of claim 12, wherein said piezoelectric element is a quartz crystal.

18. The method of claim 12, wherein said gain of said amplifier is a complex number having a magnitude and phase component, said step of causing said piezoelectric element to oscillate further comprising the step of producing a phase shift that offsets said phase component of said gain.

19. The method of claim 12, further comprising the steps of:

exposing a second piezoelectric element to said absorptive medium;

causing said second piezoelectric element to oscillate by connecting said second piezoelectric element to a second amplifier having an adjustable gain;

adjusting the gain of said second amplifier in response to variations in said absorptive medium;

producing a signal indicative of the frequency of oscillation of said second piezoelectric element;

producing a signal indicative of the adjustment made to the gain of said second amplifier; and analyzing said signals indicative of the frequency of oscillation of said second piezoelectric element and the adjustment to the gain of said second amplifier to determine a second characteristic of interest exhibited by said absorptive medium.

20. The method of claim 19, wherein said first characteristic of interest is influenced by said second characteristic of interest, further comprising the step of eliminating the influence of said second characteristic of interest.

21. The system of claim 4, wherein said viscosity-density product is determined in accordance with the expression:

$$m_\delta = \pi^{-1} 8(\mu\rho/2\omega)^{0.5}$$

where:

$\mu\rho$ = the viscosity-density product;

$m_\delta$ = the effective areal mass density of said medium; and $\omega$ = the frequency of oscillation of said piezoelectric element.

22. The system of claim 21, wherein the effective areal mass density of said medium, $m_\delta$, is determined in accordance with the expression:

$$m_\delta = -\Delta\omega/s$$

where:

$\Delta\omega$ = the shift in the frequency of oscillation of said piezoelectric element produced by the apparent mass effect of said medium; and s = a parameter representative of the material and geometry of said piezoelectric element.

23. The system of claim 1, wherein said processing means further determines the existence of potential of zero charge conditions corresponding to minimum electrokinetic coupling between said piezoelectric element and said energy-absorptive medium of interest.

24. The system of claim 6, wherein the effect said fluid has on the mass of said piezoelectric element includes the true mass effect of said fluid upon said piezoelectric element, corrected for the apparent mass effect of said fluid upon said piezoelectric element.

25. The method of claim 14, wherein said viscosity-density product is determined in accordance with the expression:

$$m_\delta = \pi^{-1}(\mu\rho/2\omega)^{0.5}$$

where:

$\mu\rho$ = the viscosity-density product;

$m_\delta$ = the effective areal mass density of said medium; and $\omega$ = the frequency of oscillation of said piezoelectric element.

26. The method of claim 25, wherein the effective areal mass density of said medium, $m_\delta$, is determined in accordance with the expression:

$$m_\delta = -\Delta\omega/s$$

where:

$\Delta\omega$ = the shift in the frequency of oscillation of said piezoelectric element produced by the apparent mass effect of said medium; and s = a parameter representative of the material and geometry of said piezoelectric element.

27. The method of claim 12, wherein said step of analyzing said signals is further performed to determine the existence of potential of zero charge conditions corresponding to minimum electrokinetic coupling between said piezoelectric element and said energy-absorptive medium of interest.

28. The method of claim 16, wherein the effect said fluid has on the mass of said piezoelectric element includes the true mass effect of said fluid upon said piezoelectric element, corrected for the apparent mass effect of said fluid upon said piezoelectric element.

* * * * *

UNITED STATES PATENT AND TRADEMARK OFFICE
CERTIFICATE OF CORRECTION

PATENT NO. : 4,783,987

DATED : November 15, 1988

INVENTOR(S) : Harold H. Hager et al.

It is certified that error appears in the above-identified patent and that said Letters Patent is hereby corrected as shown below:

| | |
|---|---|
| Column 1, line 32: | "of" (1st occurr.) should be --a-- |
| Column 1, line 35: | "suoject" should be --subjected-- |
| Column 2, lines 13 and 14: | "crystal-'impedance: should be --crystal's impedance-- |
| Column 2, line 27: | "is" should be --are-- |
| Column 5, line 17: | "simulaneously" should be --simultaneously-- |
| Column 5, line 19: | "expect" should be --except-- |
| Column 6, line 42: | "cpacitance" should be --capacitance-- |
| Column 7, line 38: | "eve" should be --even-- |
| Column 8, line 17: | "N" should be --H-- |
| Column 8, line 34: | "ip" should be subscripted to align with "xz" |
| Column 8, line 41: | "-Sm$\delta$ " should be ---Sm$_\delta$ -- |
| Column 8, line 60: | "relative" should be --relatively-- |
| Column 8, line 62: | "crried" should be --carried-- |
| Column 9, line 38: | "-k$_1$ ($\Delta$ ($\rho\mu$ )$^{0.5}$" should be ---k$_1$ $\Delta(\rho \mu)^{0.5}$-- |
| Column 10, line 51: | "a" should be --A-- |
| Column 10, line 66: | "equal" should be --equals-- |
| Column 11, line 21: | "R$_3$" (second occurrence) should be --R$_E$-- |
| Column 12, line 60: | "averge" should be --average-- |
| Column 15, line 46: | "varios" should be --various-- |

UNITED STATES PATENT AND TRADEMARK OFFICE
CERTIFICATE OF CORRECTION

PATENT NO. : 4,783,987

DATED : November 15, 1988

INVENTOR(S) : Harold H. Hager et al.

It is certified that error appears in the above-identified patent and that said Letters Patent is hereby corrected as shown below:

Column 16, line 47:         "clai" should be --claim--

Column 17, line 64:         "8" should be --(--

Signed and Sealed this

Nineteenth Day of December, 1989

Attest:

JEFFREY M. SAMUELS

*Attesting Officer*         *Acting Commissioner of Patents and Trademarks*

UNITED STATES PATENT AND TRADEMARK OFFICE
CERTIFICATE OF CORRECTION

PATENT NO. : 4,783,987
DATED : November 15, 1988
INVENTOR(S) : Harold H. Hager et al.

It is certified that error appears in the above-identified patent and that said Letters Patent is hereby corrected as shown below:

| COLUMN | LINE | |
|---|---|---|
| 1 | 4 | Insert --This invention was made with government support under grant number ISI-84-15075 awarded by the National Science Foundation. The government has certain rights in the invention.-- |

Signed and Sealed this

Twenty-eighth Day of September, 1993

Attest:

BRUCE LEHMAN

Attesting Officer

Commissioner of Patents and Trademarks